(12) United States Patent
Huber

(10) Patent No.: US 10,905,673 B2
(45) Date of Patent: Feb. 2, 2021

(54) LIPIDIC FURAN, PYRROLE, AND THIOPHENE COMPOUNDS FOR USE IN THE TREATMENT OF ATROPHIC VAGINITIS

(71) Applicant: Avoscience, LLC, Hayden, ID (US)

(72) Inventor: Samuel Richard Huber, Liberty Lake, WA (US)

(73) Assignee: Avoscience, LLC, Sheridan, WY (US)

( * ) Notice: Subject to any disclaimer, the term of this patent is extended or adjusted under 35 U.S.C. 154(b) by 0 days.

(21) Appl. No.: 16/424,335

(22) Filed: May 28, 2019

(65) Prior Publication Data

US 2019/0274994 A1    Sep. 12, 2019

Related U.S. Application Data

(63) Continuation of application No. 15/499,419, filed on Apr. 27, 2017, now abandoned.

(60) Provisional application No. 62/328,180, filed on Apr. 27, 2016.

(51) Int. Cl.
| | | |
|---|---|---|
| A61K 31/341 | (2006.01) | |
| C07D 307/36 | (2006.01) | |
| A61P 15/02 | (2006.01) | |
| A61K 9/48 | (2006.01) | |
| A61K 47/44 | (2017.01) | |
| A61K 9/00 | (2006.01) | |
| A61K 9/02 | (2006.01) | |
| A61K 31/381 | (2006.01) | |
| A61K 31/40 | (2006.01) | |
| A61K 45/06 | (2006.01) | |

(52) U.S. Cl.
CPC .......... *A61K 31/341* (2013.01); *A61K 9/0014* (2013.01); *A61K 9/0034* (2013.01); *A61K 9/02* (2013.01); *A61K 9/4875* (2013.01); *A61K 31/381* (2013.01); *A61K 31/40* (2013.01); *A61K 45/06* (2013.01); *A61K 47/44* (2013.01); *A61P 15/02* (2018.01); *C07D 307/36* (2013.01)

(58) Field of Classification Search
CPC .. A61K 31/341; A61K 9/0014; A61K 9/0034; A61K 9/02; A61K 9/4875; A61K 31/381; A61K 31/40; A61K 45/06; A61K 47/44; A61P 15/02; C07D 307/36
See application file for complete search history.

(56) References Cited

U.S. PATENT DOCUMENTS

| | | |
|---|---|---|
| 3,590,028 A | 6/1971 | Arcamone et al. |
| 4,427,693 A | 1/1984 | Haber |
| 5,082,856 A | 1/1992 | Taniguchi et al. |
| 5,468,490 A | 11/1995 | Huber et al. |
| 5,514,709 A | 5/1996 | Counts et al. |
| 6,582,688 B1 | 6/2003 | Broutin et al. |
| 6,960,594 B2 | 11/2005 | Labrecque et al. |
| 7,037,937 B2 | 5/2006 | Uckun |
| 7,375,105 B2 | 5/2008 | Dean et al. |
| 7,589,121 B2 | 9/2009 | Piccirilli et al. |
| 9,371,302 B2 | 6/2016 | Huber |
| 2004/0018258 A1 | 1/2004 | Piccirilli et al. |
| 2005/0004211 A1 | 1/2005 | Wu et al. |
| 2005/0124684 A1 | 6/2005 | Du et al. |
| 2006/0003033 A1 | 1/2006 | McClellan et al. |
| 2006/0018937 A1 | 1/2006 | Friedman et al. |
| 2008/0081837 A1 | 4/2008 | Piccirilli et al. |
| 2008/0219937 A1 | 9/2008 | Msika et al. |
| 2013/0183289 A1 | 7/2013 | Gorelik et al. |
| 2016/0263080 A1 | 9/2016 | Huber |
| 2018/0050013 A1 | 2/2018 | Huber |

FOREIGN PATENT DOCUMENTS

| | | |
|---|---|---|
| FR | 2678614 | 3/1991 |
| JP | 2008-501003 A | 1/2008 |
| JP | 2008-501004 A | 1/2008 |
| WO | WO 2007/032591 A1 | 3/2007 |
| WO | WO 2008/080986 A1 | 7/2008 |
| WO | WO 2014/160940 A2 | 10/2014 |

OTHER PUBLICATIONS

As archived Mar. 2012 available at "Avogen: The first and only supplement for the extracellular matrix (ECM)".
Biglia et al., "Low-dose vaginal estrogens or vaginal moisturizer in breast cancer survivors with urogenital atrophy: a preliminary study," Gynecological Endocrinology, Jun. 2010; 26(6): 404-412.
Buu_Hoi et al., "Thiophen derivatives of potential biological interest. Part IV. Tuberculostatic thiophen compounds" J. Chem. Soc., 1953; 547-549.
Cailleau, R. et al., "Long-term human breast carcinoma cell lines of metastatic origin: preliminary characterization" In Vitro, 1978; 14: 911-915.
Ghumman "Atrophic Vaginitis: Diagnosis and Treatment" (J. South Asian Federation of Menopause Societies, Jan.-Jun. 2013; 1(1): p. 4-12).
Farage, et al., "The vulvar epithelium differs from the skin: implications for cutaneous testing to address topical vulvar exposures," Contact Dermatitis 2004: 51: 201-209.
Hackett et al., "Two syngeneic cell lines from human breast tissue: the aneuploid mammary epithelial (Hs 578T) and the diploid myoepithelial (Hs 578Bst) cell lines" J. Natl. Cancer Inst., 1977; 58: 1795-1806.

(Continued)

*Primary Examiner* — Robert H Havlin
(74) *Attorney, Agent, or Firm* — Knowles Intellectual Property Strategies, LLC

(57) ABSTRACT

Provided herein are lipidic furan, pyrrole, and thiophene compounds, compositions, and methods using such compounds and compositions for the treatment of atrophic vaginitis. Specifically, the invention includes administering an effective amount of a compound of Formula I, I', or I", or a pharmaceutically acceptable composition, salt, isotopic analog, prodrug, or combination thereof, to a subject suffering from atrophic vaginitis.

2 Claims, 1 Drawing Sheet

(56) References Cited

OTHER PUBLICATIONS

Figure 1A:
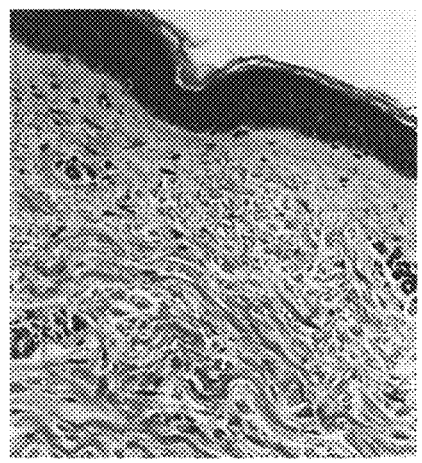
Figure 1B:
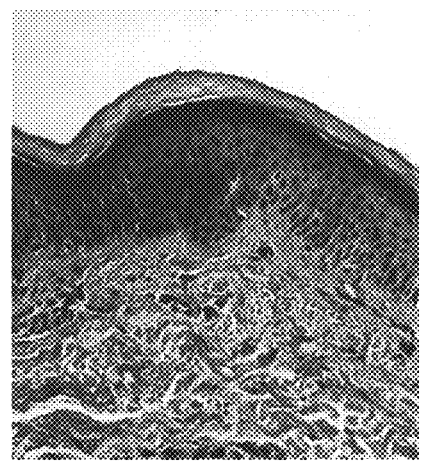

Huffstutter, J.E. et al. "Scleroderma as Fibrotic Disorder" in Immunology of Rheumatic Diseases, Jan. 1, 1985, Springer (ISBN: 978-1-4613-2493-5), 397-423.
International Search Report and Written Opinion for PCT/US2017/029875.
Kashman, Y. et al., "New Compounds from Avocado Pear" Tetrahedron, 1969; 25: 4617-4631.
Kashman, Y. et al., "Six New C17-olefinic and Acetylenic Oxygenated Compounds from Avocado Pear" Israel Journal of Chemistry, 1969; 7: 173-176.
Laczko et al. "Active lysyl oxidase (LOX) correlates with FAK/paxillin activation and migration in invasive astrocytes" Neuropathol Appl Neurobiol., 2007; 33: 631-643.
Legares, D. et al, "Targeting Focal Adhesion Kinase in Fibrotic Diseases" BioDrugs. 2013, 27(1), 15-23.
Legares, D. et al, "Inhibition of focal adhesion kinase prevents experimental lung fibrosis and myofibroblast formation" Arthritis Rheum. 2012, 64(5), 1653-1664.
Mohamed et al., "Synthesis of mycalazol and mycalazal analogs with potent antiproliferating activities" Pure Appl. Chem., 2011; 83(3): 489-493.
Muller et al. "Single-step induction of mammary adenocarcinoma in transgenic mice bearing the activated c-neu oncogene" Cell, 1988; 54: 105-115.
Neeman, I. et al., "New antibacterial agent isolated from the avocado pear" Appl. Microbiol., 1970; 19: 470-473.
Papireddy, K. et al., "Antimalarial Activity of Natural and Synthetic Prodiginines" J. Med. Chem., 2011; 54: 5296-5306.
Payne et al., "Lysyl oxidase regulates breast cancer cell migration and adhesion through a hydrogen peroxide-mediated mechanism" Cancer Res., 2005; 65: 11429-11436.
PUBCHEM. Compound Summary for CID 8029, Create Date: Sep. 16, 2004. [retrieved on Oct. 15, 2014]. Retrieved from the internet. <URL: https://pubchem.ncbi.nlm.nih.gov/summary/summary.cgi?cid=8029&loc=ec_rcs>.
Rodriguez-Saona C. et al., "Avocadofurans and Their Tetrahydrofuran Analogues: Comparison of Growth Inhibitory and Insecticidal Activity", J. Agric. Food Chem., 2000; 48: 3642-3645.
Rodriguez-Saona C. et al., "Novel Antifeedant and Insecticidal Compounds from Avocado Idioblast Cell Oil" J. Chem. Ecol., 1998, 24: 867-889.
Toxicology and carcinogenesis studies of furan (CAS No. 110-00-9) in F344/N Rats and B6C3F1 mice (gavage studies). National Toxicology Program Technical Report Series No. 402, Jan. 1993. [retrieved on Oct. 15, 2014]. Retrieved from the Internet. <URL: http://ntp.niehs.nih.gov/ntp.htdocs.lt_rpts/tr402.pdf>.
Meotti et al., "Thiophenes and furan derivatives: s anew class of potential pharmacological agents,", Environmental Toxicology and Pharmacology 37, 2003, pp. 37-44.
U.S. Pat. No. 9,371,302, B2, U.S. Appl. No. 14/229,130, Huber, filed Jan. 21, 2016.
U.S. Pat. No. 9,814,694, B2, U.S. Appl. No. 15/162,074, Huber, filed Nov. 14, 2017.
US, 2017/0312246, A1, U.S. Appl. No. 15/499,419, Huber, filed Nov. 2, 2017.
US, 2018/0050013, A1, U.S. Appl. No. 15/782,535, Huber, filed Feb. 22, 2018.

Vehicle

Treated (Formula I(n))

LIPIDIC FURAN, PYRROLE, AND THIOPHENE COMPOUNDS FOR USE IN THE TREATMENT OF ATROPHIC VAGINITIS

RELATED APPLICATION

This application is a continuation of U.S. application Ser. No. 15/499,419, filed Apr. 24, 2017, and which claims priority to provisional U.S. Application No. 62/328,180, filed Apr. 27, 2016. The entirety of each of these applications is hereby incorporated by reference for all purposes.

FIELD OF THE INVENTION

The present invention is directed to oral and topical dosed compounds, methods, and compositions for the treatment of atrophic vaginitis.

BACKGROUND

Atrophic vaginitis, also known as vaginal atrophy or vulvovaginal atrophy, is a common disorder affecting up to 45% of postmenopausal woman. (See Goldstein et al., Multidisciplinary Overview of Vaginal Atrophy and Associated Genitourinary Symptoms in Postmenopausal Women, Sex Med 2013; 1:44-53). Women experiencing atrophic vaginitis often present with both sexual and nonsexual or urologic complications due to a reduction in the production of estrogen, which affects many organs including the genitourinary system. Typically, women with atrophic vaginitis experience vaginal dryness, post-coital bleeding, soreness, loss of sexual arousal and libido, itching, irritation, burning, vulvar pruritus, and dyspareunia. Urinary symptoms associated with atrophic vaginitis include urgency, increased frequency, nocturia, dysuria, incontinence, and recurrent urinary tract infection (RUTI). Many women with atrophic vaginitis experience significant personal distress due to the pain associated with the disorder, the inconvenience associated with the urological symptoms, and the potential interruption in personal relationships associated with the resultant sexual dysfunction. Nonetheless, it is estimated that only 25% of women with atrophic vaginitis seek treatment for the disorder (see Melta et al., Vulvovaginal complaints, Clinical Obstetrics and Gynecology, 2008; 51:549-550).

Current modalities for the treatment of atrophic vaginitis generally revolve around the use of hormonal agents. For hormonal treatments, medications containing the female hormone estrogen have been widely prescribed, both systemically (oral and parenteral forms) and in topical applications, including creams, vaginal rings, and vaginal tablets (see Goldstein et al., Multidisciplinary Overview of Vaginal Atrophy and Associated Genitourinary Symptoms in Postmenopausal Women, Sex Med 2013; 1:44-53). Unfortunately, the use of estrogen containing medications have significant drawbacks, including the increased risk of developing estrogen dependent neoplasms, breast sensitivity, nausea and vomiting, vaginal bleeding, and pain in the perineal area. (see, Suckling et al, Local oestrogen for vaginal atrophy in postmenopausal women, Cochrane Database Syst Rev 2006; (4); CD001500). The use of topical applications, while reducing the risks of systemic exposure, also are not without side effects including the development of hyperplasia and endometrial thickening (see Goldstein et al., Multidisciplinary Overview of Vaginal Atrophy and Associated Genitourinary Symptoms in Postmenopausal Women, Sex Med 2013; 1:44-53).

Due to the associated side effects with the use of estrogen, the U.S. Federal Drug Authority (FDA) has suggested that women considering such therapy fully understand the inherent risks and should discuss with their physicians whether the benefits outweigh the risks, as postmenopausal women taking estrogen have an increased risk of stroke, and women taking estrogen with progestin have an increased risk of breast cancer, uterine cancer, stroke, heart attack, blood clots, dementia, gallbladder disease, and ovarian cancer.

In regard to furan derivatives, Kashman et al. first reported the avocadofurans as a new class of phytochemicals. See, Kashman, Y, et al., "New Compounds from Avocado Pear", Tetrahedron, 25:4617-4631 (1969) and Kashman, Y, et al., "Six New C17-olefinic and Acetylenic Oxygenated Compounds from Avocado Pear", Isr. J. Chem., 7:173-176. The authors isolated 2-(trideca-12-ynyl)furan and 2-(trideca-12-enyl)furan from P. americana fruit and seeds. Magalhaes et al. subsequently identified several other 2-alkylfurans with $C_{13}$ mono- and diunsaturated side chains from methanol extracts of avocado seeds [Persea gratissima Gartn. (syn. P. americana)] from Brazil. See, Magalhaes et al., "The avocatins—a new class of natural products", An. Acd. Bras. Cienc. 42(suppl):45-48 (1970).

U.S. Pat. No. 5,468,490 to Huber, S. R. and Counts, D. F. discloses the lipidic furan, 17-(2-furanyl-8-11-cis-cis-heptadecadiene, also referred to as 2-(8Z,11Z-heptadecadienyl) furan).

U.S. Pat. No. 5,514,709 to Counts, D. F. and Huber, R. discloses lipid furans, 2-alkyl furans, and their specificity to types I and III collagen.

Rodriguez-Saona, C. et al. discloses the synthesis of 2-(pentadecyl)furan and 2-(heptadecyl)furan. See, Rodriquez-Saona, C., et al., "Avocadofurans and Their Tetrahydrofuran Analogues: Comparison of Growth Inhibitory and Insecticidal Activity", J. Agric. Food Chem., 48:3642-3645 (2000).

U.S. Pat. Application No. 2004/0018258 to Piccirilli, A. and Legrand, J. discloses the process for obtaining a furan lipid-rich unsaponifiable material from avocado.

U.S. Pat. Application No. 2008/0219937 to Msika, P. and Piccardi, N. discloses the use of a cosmetic composition with depigmenting or lightening action comprising as active at least one 2-alkyl furan.

U.S. Pat. Application No. 2008/0081837 to Piccirilli, A., et a., disclose a method for preventing and/or treating diabetes using 2-alkyl furans wherein the 2-position is substituted with a $C_1$-$C_{35}$ alkyl, $C_1$-$C_{35}$ alkenyl, or $C_1$-$C_{35}$ alkynyl substituent.

U.S. Pat. No. 7,589,121 to Piccirilli, A. et al., discloses the use of alkyl furans for the treatment of obesity.

U.S. Pat. Publication No. 2013/0183289 to Gorelik, L. et al discloses the use avacadanofuran for the treatment of a DNA virus.

U.S. Pat. Publication No. 2014/0309274 describes the use of lipic furan, pyrrole, and thiophene compounds for treating neoplastic, fibrotic, and neurological disorders.

In regard to pyrroles, U.S. Pat. No. 5,082,856 to Taniguchi, M. et al discloses pyrrolecarboxylic acid derivatives for the treatment of hyperlipemia and arteriosclerosis. The authors disclose the synthesis of 2,5-disubstituted, and 2,4-disubstited pyrroles.

Mycalazol and mycalazal analogs having antiproliferating activity been disclosed by Mohamed, Y. M. A. and Hansen, T. V. See, Mohamed, Y. M. A. and Hansen, T. V., "Synthesis of mycalazol and mycalazal analogs with potent antiproliferating activities", Pure Appl. Chem., 83(3):489-493 (2011).

Papireddy, K. et al. disclosed the antimalarial activity of prodiginines. See, Papireddy, K. et al., "Antimalarial Activity of Natural and Synthetic Prodiginines", J. Med. Chem., 54:5296-5306 (2011).

In regard to thiophene derivatives, 2,5-disubstituted thiophene analogs were disclosed by Buu-Hoi, N. P, et al. as potential tuberculostatic compounds. See, Buu-Hoi et al., "The Thiourea Type of Tuberculostatic Compounds and Their Mechanism of Action," Comptes Rendus Chimie, vol. 237, pp. 498-500 (1953).

Accordingly, there is a continuing need to identify new treatments to target atrophic vaginitis that provide for the renormalization of vaginal tissue activity, restores vaginal elasticity, assists with vaginal moisture, normalizes sensation, and eliminates discomfort without exposing the patient to added estrogenic activity.

SUMMARY

Provided herein are lipidic furan, pyrrole, and thiophene compounds, compositions, and methods using such compounds and compositions for the treatment of atrophic vaginitis. Specifically, the invention includes administering an effective amount of a compound of Formula I, I', or I", or a pharmaceutically acceptable composition, salt, isotopic analog, prodrug, or combination thereof, to a subject suffering from atrophic vaginitis, wherein Formula I, I', or I" are:

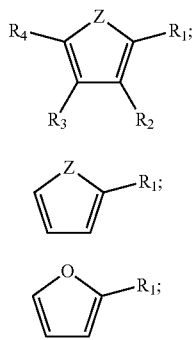

wherein;
each Z is independently O, S or $NR_5$;
wherein $R_1$, $R_2$, $R_3$ and $R_4$, are the same or different, separately represent a hydrogen atom, a $C_1$-$C_{35}$ alkyl radical, advantageously $C_{10}$-$C_{22}$, more advantageously $C_{12}$-$C_{20}$, further advantageously $C_{13}$-$C_{17}$; a $C_1$-$C_{35}$ alkenyl radical, advantageously $C_{10}$-$C_{22}$, more advantageously $C_{12}$-$C_{20}$, further advantageously $C_{13}$-$C_{17}$; or a $C_1$-$C_{35}$ alkynyl radical, advantageously $C_{10}$-$C_{22}$, more advantageously $C_{12}$-$C_{20}$, further advantageously $C_{13}$-$C_{17}$, and wherein the alkyl, alkenyl or alkynyl moiety is optionally substituted with one or more halogens (F, Cl, Br, or I, and more typically F) and/or by one or more moieties selected from the group consisting of epoxy (e.g., an oxygen divalently linked to the carbon chain), hydroxyl or protected hydroxyl ($OR_5$), thiol or protected thiol ($SR_5$), amine ($NR_5R_6$), aldehyde (—CHO), ketone (—$COR_5$), acetyl (—O—CO—$R_5$), or ester (—C(O)$OR_5$) function and wherein $R_5$ and $R_6$ separately represent a hydrogen atom, a $C_1$-$C_{35}$, more typically a $C_1$ to $C_{20}$ alkyl radical, advantageously $C_{10}$-$C_{22}$, more advantageously $C_{12}$-$C_{20}$, further advantageously $C_{13}$-$C_{17}$, or a $C_1$-$C_{35}$ alkenyl radical, advantageously $C_{10}$-$C_{22}$, more advantageously $C_{12}$-$C_{20}$, or further advantageously $C_{13}$-$C_{17}$.

In one embodiment $C_1$-$C_{35}$ alkenyl is $C_2$-$C_{35}$ alkenyl.
In one embodiment $C_1$-$C_{35}$ alkynyl is $C_2$-$C_{35}$ alkynyl.
In one embodiment, $R_1$ is a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ saturated carbon chain. In another embodiment, $R_1$ is a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ carbon chain optionally with one, two, or three double or triple bonds, or a combination thereof. In one embodiment, the $R_1$ has one, two, or three double bonds, and wherein the two double bonds can be conjugated or non-conjugated and wherein the three double bonds can be fully, partially, or non-conjugated. In one embodiment, a double bond can be in the terminal position. In another embodiment, $R_1$ is a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ carbon chain with at least one double and at least one triple bond. In yet another embodiment, $R_1$ is a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ carbon chain with one triple bond. In one embodiment, the triple bond can be in the terminal position.

In one embodiment, $R_1$ is a $C_{11-25}$ saturated carbon chain. In one embodiment, $R_1$ is a $C_{13}$-$C_{17}$ saturated carbon chain. In one embodiment, $R_1$ is a $C_{11}$, $C_{13}$, $C_{15}$, $C_{17}$, $C_{19}$, $C_{21}$, $C_{23}$, or $C_{25}$ saturated carbon chain. In another embodiment, $R_1$ is a $C_{11}$, $C_{13}$, $C_{15}$, $C_{17}$, $C_{19}$, $C_{21}$, $C_{23}$, or $C_{25}$ carbon chain optionally with one, two, or three double or triple bonds or a combination thereof.

In one embodiment, the $R_1$ has one, two, or three double bonds, and wherein the two double bonds can be conjugated or non-conjugated and wherein the three double bonds can be fully, partially or non-conjugated. In one embodiment, a double bond can be in the terminal position. In another embodiment, $R_1$ is a $C_{11}$, $C_{13}$, $C_{15}$, $C_{17}$, $C_{19}$, $C_{21}$, $C_{23}$, or $C_{25}$ carbon chain with at least one double and at least one triple bond. In yet another embodiment, $R_1$ is a $C_{11}$, $C_{13}$, $C_{15}$, $C_{17}$, $C_{19}$, $C_{21}$, $C_{23}$, or $C_{25}$ carbon chain with one triple bond. In one embodiment, the triple bond can be in the terminal position.

The double bond can be in the Z or E configuration. In one embodiment, $R_1$ has one or two double bonds in the Z configuration. In an alternative embodiment, one or two double bonds are in the E configuration. For example, when conjugated, the double bonds can be: (2Z, 5Z); (3Z, 6Z), (7Z, 10Z), (8Z, 11Z), (8Z, 11Z), (8Z, 10Z), (9Z, 12Z), (10Z, 13Z), (11Z, 14Z), or (12Z, 15Z). In an alternative embodiment, $R_1$ has a single double bond in the Z configuration. In one embodiment, the double bond can be (2Z), (3Z), (4Z), (5Z), (6Z), (7Z), (8Z), (9Z), (10Z), (11Z), (12Z), (13Z), (14Z), (15Z), (16Z), (17Z), (18Z), or (19Z). In one embodiment, $R_1$ has a single double bond in the E configuration. In one embodiment, the double bond can be (2E), (3E), (4E), (5E), (6E), (7E), (8E), (9E), (10E), (11E), (12E), (13E), (14E), (15E), (16E), (17E), (18E), or (19E). In one embodiment, the double bonds can be: (2Z, 5E); (3Z, 6E), (7Z, 10E), (8Z, 10E), (8Z, 11E), (9Z, 12E), (10Z, 13E), (11Z, 14E), or (12Z, 15E). In one embodiment, the double bonds can be: (2E, 5Z); (3E, 6Z), (7E, 10Z), (8E, 11Z), (9E, 11Z), (9E, 12Z), (10E, 13Z), (11E, 14Z), or (12E, 15Z).

In one embodiment, $R_1$ is substituted with at least one $OR_5$ group. In one sub-embodiment, $R_1$ is substituted with at least one $OR_5$ group wherein $R_5$=H.

In one embodiment, $R_1$ is substituted with at least two $OR_5$ groups. In one sub-embodiment, $R_1$ is substituted with at least two $OR_5$ groups wherein $R_5$=H.

In one embodiment, $R_1$ is substituted with at least three $OR_5$ groups. In one sub-embodiment, $R_1$ is substituted with at least three $OR_5$ groups wherein $R_5$=H.

In one embodiment, $R_1$ is substituted with at least one $OR_5$ group. In one sub-embodiment, $R_1$ is substituted with at least one $OR_5$ group wherein $R_5$=C(O)CH$_3$.

In one embodiment, $R_1$ is substituted with at least two $OR_5$ groups. In one sub-embodiment, $R_1$ is substituted with at least two $OR_5$ groups wherein $R_5$=C(O)CH$_3$.

In one embodiment, $R_1$ is substituted with at least three $OR_5$ groups. In one sub-embodiment, $R_1$ is substituted with at least three $OR_5$ groups wherein $R_5$=C(O)CH$_3$.

In one embodiment, $R_1$ is substituted with at least one $NR_5R_6$ group. In one sub-embodiment, $R_1$ is substituted with at least one $NR_5R_6$ group wherein $R_5$=$R_6$=H.

In one embodiment, $R_1$ is substituted with at least two $NR_5R_6$ groups. In one sub-embodiment, $R_1$ is substituted with at least two $NR_5R_6$ groups wherein $R_5$=$R_6$=H.

In one embodiment, $R_1$ is substituted with at least three $NR_5R_6$ groups. In one sub-embodiment, $R_1$ is substituted with at least three $NR_5R_6$ groups wherein $R_5$=$R_6$=H.

In one embodiment, $R_1$ is $CH_3$—$(CH_2)_m$—$(CH=CH)_x$—$(CH_2)_m$ wherein n, m, and x do not equal 0 and m+2x+n=1 to 35.

In some embodiments, the compound has Formula I:

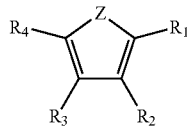

wherein;
Z is independently O, S, $NR_5$;
$R_1$=$R_2$=$R_3$=H;
$R_4$ is a $C_9$-$C_{20}$ alkyl chain comprising two or more double bonds optionally substituted as defined above.

In some embodiments, the compound has Formula I':

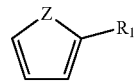

wherein;
$R_1$ is a $C_9$-$C_{20}$ alkyl chain comprising two or more double bonds optionally substituted as defined above.

In some embodiments, the compound has Formula I":

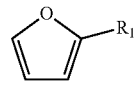

wherein;
$R_1$ is a $C_9$-$C_{20}$ alkyl chain comprising two or more double bonds optionally substituted as defined above.

In an alternative embodiment, the furan, thiophene, or pyrrole can be fused to another heterocyclic or heteroaromatic moiety to produce a multi-ring core, for example, benzofuran, benzothiophene, or indole, which may optionally be substituted with one or more functional groups, preferably with one or more alkyl, alkoxy, halo, or hydroxy substituents.

In one embodiment, a compound of Formula I, Formula I', or Formula I" has a purity of greater than 95%, greater than 96%, greater than 97%, greater than 98%, or greater than 99%.

Accordingly, in one aspect of the present invention, provided herein is a method of treating atrophic vaginitis, comprising administering an effective amount of a compound of Formula I, I', I", or a pharmaceutically acceptable composition, salt, isotopic analog, prodrug, or combination thereof. In one embodiment, the compound administered is selected from a compound of any of I(a)-I(m). In one embodiment, the compound administered is selected from a compound of Table 1. In one embodiment, the compound administered is selected from the group consisting of Compound I(n), Compound I(ap), or Compound I(aq).

TABLE 1

| | |
|---|---|
| Formula I(n) | ![structure] |
| Formula I(o) | ![structure] |
| Formula I(p) | ![structure] |
| Formula I(q) | ![structure] |
| Formula I(r) | ![structure] $(CH_2)_{11}$—$\underset{H}{C}$=$CH_2$ |
| Formula I(s) | ![structure] $(CH_2)_{11}$—C≡CH |

TABLE 1-continued

| Formula I(t) | 2-thienyl–(CH₂)₉–CH=CH–CH=CH–(CH₂)₄–CH₃ |
| Formula I(u) | 2-pyrrolyl(NH)–(CH₂)₉–CH=CH–CH=CH–(CH₂)₄–CH₃ |
| Formula I(v) | 2-furyl–(CH₂)₁₄–CH₃ |
| Formula I(w) | 2-furyl–CH=CH–(CH₂)₁₁–CH=CH₂ |
| Formula I(x) | 2-furyl–CH=CH–(CH₂)₁₃–CH₃ |
| Formula I(y) | 2-furyl–CH=CH–(CH₂)₇–CH=CH–CH=CH–(CH₂)₄–CH₃ |
| Formula I(z) | 2-thienyl–(CH₂)₁₄–CH₃ |
| Formula I(aa) | 2-thienyl–(CH₂)₁₂–CH=CH₂ |
| Formula I(ab) | 2-thienyl–(CH₂)₁₂–C≡CH |
| Formula I(ac) | 2-thienyl–CH=CH–(CH₂)₁₁–CH=CH₂ |
| Formula I(ad) | 2-thienyl–CH=CH–(CH₂)₁₃–CH₃ |
| Formula I(ae) | 2-thienyl–(CH₂)₁₆–CH₃ |
| Formula I(af) | 2-thienyl–CH=CH–(CH₂)₁₅–CH₃ |
| Formula I(ag) | 2-thienyl–CH=CH–(CH₂)₇–CH=CH–CH=CH–(CH₂)₄–CH₃ |
| Formula I(ah) | 2-pyrrolyl(NH)–(CH₂)₁₄–CH₃ |
| Formula I(ai) | 2-pyrrolyl(NH)–(CH₂)₁₂–CH=CH₂ |

TABLE 1-continued

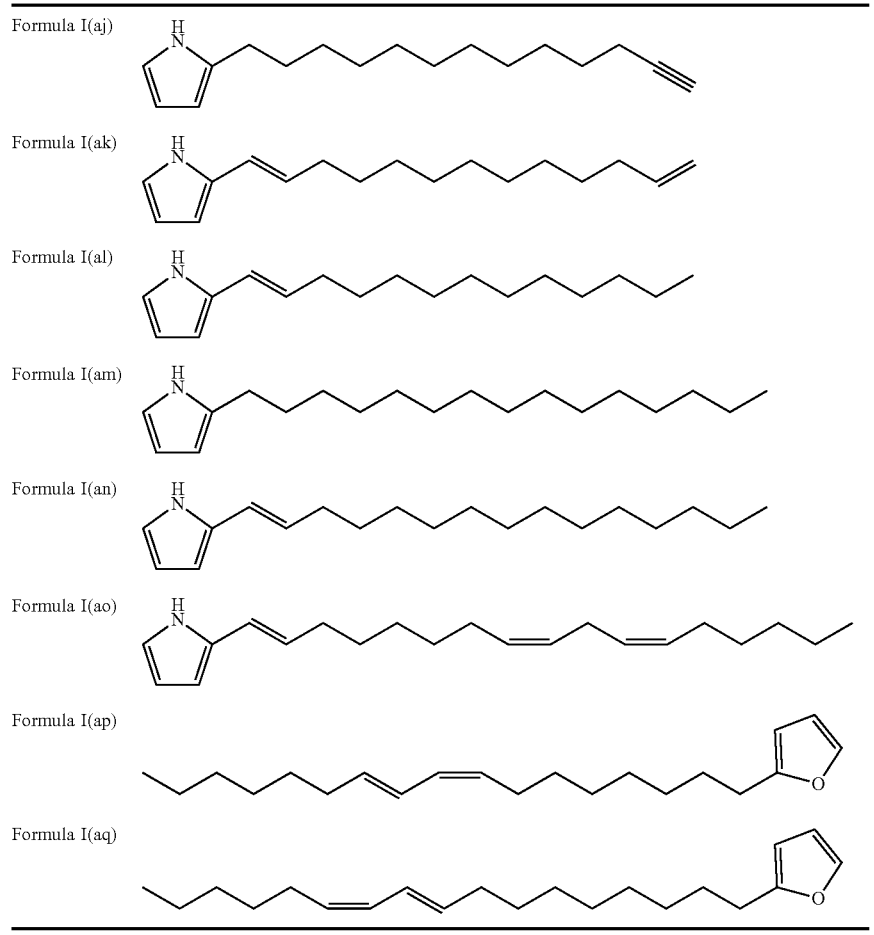

| | |
|---|---|
| Formula I(aj) | |
| Formula I(ak) | |
| Formula I(al) | |
| Formula I(am) | |
| Formula I(an) | |
| Formula I(ao) | |
| Formula I(ap) | |
| Formula I(aq) | |

In one embodiment of the present invention, provided herein is a method of reducing at least one symptom associated with atrophic vaginitis, comprising administering an effective amount of a compound of Formula I, I', or I", or a pharmaceutically acceptable composition, salt, isotopic analog, prodrug, or combination thereof. In one embodiment, the compound administered is selected from a compound of any of I(a)-I(m). In one embodiment, the compound administered is selected from a compound of Table 1. In one embodiment, the compound administered is selected from the group consisting of Compound I(n), Compound I(ap), or Compound I(aq).

In one embodiment provided herein is a method of renormalizing vaginal tissue deteriorated as a result of atrophic vaginitis, comprising administering an effective amount of a compound of Formula I, I', or I", or a pharmaceutically acceptable composition, salt, isotopic analog, prodrug, or combination thereof. In one embodiment, the compound administered is selected from a compound of any of I(a)-I(m). In one embodiment, the compound administered is selected from a compound of Table 1. In one embodiment, the compound administered is selected from the group consisting of Compound I(n), Compound I(ap), or Compound I(aq).

In one embodiment of the present invention, provided herein is a method of preventing atrophic vaginitis, comprising administering an effective amount of a compound of Formula I, I', or I", or a pharmaceutically acceptable composition, salt, isotopic analog, prodrug, or combination thereof. In one embodiment, the compound administered is selected from a compound of any of I(a)-I(m). In one embodiment, the compound administered is selected from a compound of Table 1. In one embodiment, the compound administered is selected from the group consisting of Compound I(n), Compound I(ap), or Compound I(aq).

In one embodiment provided herein is a method of restoring the loss of vaginal elasticity as a result of atrophic vaginitis, comprising administering an effective amount of a compound of Formula I, I', or I", or a pharmaceutically acceptable composition, salt, isotopic analog, prodrug, or combination thereof. In one embodiment, the compound administered is selected from a compound of any of I(a)-I(m). In one embodiment, the compound administered is selected from a compound of Table 1. In one embodiment, the compound administered is selected from the group consisting of Compound I(n), Compound I(ap), or Compound I(aq).

In one embodiment of the present invention, provided herein is a method of restoring the loss of vaginal lubrication as a result of atrophic vaginitis, comprising administering an effective amount of a compound of Formula I, I', or I", or a pharmaceutically acceptable composition, salt, isotopic analog, prodrug, or combination thereof. In one embodiment, the compound administered is selected from a compound of any of I(a)-I(m). In one embodiment, the compound administered is selected from a compound of Table 1. In one embodiment, the compound administered is selected from the group consisting of Compound I(n), Compound I(ap), or Compound I(aq).

In some embodiments, the subject or host is a mammal, including a human. The compound can be administered to the subject by any desired route, including intravenous, sublingual, buccal, oral, intraaortal, topical, intranasal, parenteral, transdermal, systemic, intramuscular, or via inhalation. In one embodiment, the compound is administered topically.

The compounds described herein can be administered to the subject in combination with other agents used for the treatment of atrophic vaginitis. If convenient, the compounds described herein can be administered at the same time as another agent, in order to simplify the treatment regimen. In some embodiments, the compound and the other therapeutic can be provided in a single formulation. In one embodiment, the use of the compounds described herein is combined in a therapeutic regime with other agents.

In summary, the present invention includes the following features:

A) Compounds of Formula I, I', or I" as described herein, and pharmaceutically acceptable compositions, salts, isotopic analogs, or prodrugs thereof, for use in the treatment of atrophic vaginitis in a subject. In one embodiment, the compound administered is selected from a compound of any of I(a)-I(m). In one embodiment, the compound is selected from the compounds in Table 1. In one embodiment, the compound is Compound I(n), Compound I(ap), or Compound I(aq);

B) Compounds of Formula I, I', or I" as described herein, and pharmaceutically acceptable compositions, salts, isotopic analogs, or prodrugs thereof, for use in the renormalizing vaginal tissue deteriorated as a result of atrophic vaginitis in a subject. In one embodiment, the compound administered is selected from a compound of any of I(a)-I(m). In one embodiment, the compound is selected from the compounds in Table 1. In one embodiment, the compound is Compound I(n), Compound I(ap), or Compound I(aq);

C) Compounds of Formula I, I', or I" as described herein, and pharmaceutically acceptable compositions, salts, isotopic analogs, or prodrugs thereof, for use in preventing atrophic vaginitis in a subject. In one embodiment, the compound administered is selected from a compound of any of I(a)-I(m). In one embodiment, the compound is selected from the compounds in Table 1. In one embodiment, the compound is Compound I(n), Compound I(ap), or Compound I(aq);

D) Compounds of Formula I, I', or I" as described herein, and pharmaceutically acceptable compositions, salts, isotopic analogs, or prodrugs thereof, for use in restoring the loss of vaginal elasticity as a result of atrophic vaginitis in a subject. In one embodiment, the compound administered is selected from a compound of any of I(a)-I(m). In one embodiment, the compound is selected from the compounds in Table 1. In one embodiment, the compound is Compound I(n), Compound I(ap), or Compound I(aq);

E) Compounds of Formula I, I', or I" as described herein, and pharmaceutically acceptable compositions, salts, isotopic analogs, or prodrugs thereof, for use in restoring the loss of vaginal lubrication as a result of atrophic vaginitis in a subject. In one embodiment, the compound administered is selected from a compound of any of I(a)-I(m). In one embodiment, the compound is selected from the compounds in Table 1. In one embodiment, the compound is Compound I(n), Compound I(ap), or Compound I(aq);

F) Compound I(ap), or a pharmaceutically acceptable composition, salt, isotopic analog, prodrug, or combination thereof;

G) Compound I(aq), or a pharmaceutically acceptable composition, salt, isotopic analog, prodrug, or combination thereof;

H) A compound as described herein, or a pharmaceutically acceptable composition, salt, isotopic analog, or prodrug thereof, for use in combination with a second estrogenic agent in a subject undergoing a therapeutic regime to treat atrophic vaginitis. In one embodiment, the compound administered is selected from a compound of any of I(a)-I(m). In one embodiment, the compound is selected from the compounds in Table 1. In one embodiment, the compound is Compound I(n), Compound I(ap), or Compound I(aq);

I) Use of a compound described herein, or a pharmaceutically acceptable composition, salt, isotopic analog, or prodrug thereof, in the manufacture of a medicament for use to treat atrophic vaginitis;

F) Processes for the preparation of therapeutic products that contain an effective amount of a compound described herein, for use in the treatment of a subject having atrophic vaginitis;

G) A method for manufacturing a medicament selected from the compounds described herein intended for therapeutic use in the treatment of atrophic vaginitis. Compounds of Formula I, I', or I" as described herein. In one embodiment, the compound administered is selected from a compound of any of I(a)-I(m). In one embodiment, the compound is selected from the compounds in Table 1. In one embodiment, the compound is Compound I(n), Compound I(ap), or Compound I(aq);

N) Processes for the preparation of therapeutic products that contain an effective amount of a compound described herein, for use in the treatment of a subject having atrophic vaginitis;

O) A method for manufacturing a medicament selected from the compounds described herein intended for therapeutic use as a treatment of atrophic vaginitis.

P) Compounds as described herein for use to treat atrophic vaginitis, wherein the active ingredient is not provided as a botanical extract mixture or combination, but instead the active compound is delivered in a highly pure form. In one embodiment, the invention is a dosage form for the treatment of atrophic vaginitis, wherein the active compound has a purity of at least 96%, 97%, 98%, or 99%, without respect to fillers, stabilizers, or other inert or inactive ingredients. In an alternative embodiment, the dosage form has two or more active ingredients, wherein only one of the active ingredients is selected from compounds of Formula I, I', or I" as described herein. In one embodiment, the compound administered is selected from a compound of any of I(a)-I(m). In one embodiment, the compound is selected from the compounds in Table 1. In one embodiment, the compound is Compound I(n), Compound I(ap), or Compound I(aq).

DETAILED DESCRIPTION OF THE INVENTION

The present invention concerns lipidic furan, pyrrole, and thiophene compounds, methods, and compositions for treatment of atrophic vaginitis.

Definitions

Unless otherwise stated, the following terms used in this application, including the specification and claims, have the definitions given below. As used in the specification and the appended claims, the singular forms "a," "an" and "the" include plural referents unless the context clearly dictates otherwise. Definition of standard chemistry terms may be found in reference works, including Carey and Sundberg (2007) Advanced Organic Chemistry 5th Ed. Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in March's Advanced Organic Chemistry: Reactions, Mechanisms, and Structure, 6th Edition, M. B. Smith and J. March, John Wiley & Sons, Inc., Hoboken, N.J., 2007.

The term "lipidic furan" as used herein refers a compound comprising a furan ring substituted with at least one branched, straight chain or cyclic hydrocarbon group, preferably a linear hydrocarbon chain, more preferably comprising a linear hydrocarbon chain comprising one or more ethylenic or acetylenic unsaturations.

As used herein, the term "prodrug" means a compound which when administered to a host in vivo is converted into the parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

Throughout the specification and claims, a given chemical formula or name shall encompass all optical and stereoisomers, as well as racemic mixtures where such isomers and mixtures exist, unless otherwise noted.

The subject treated is typically a human subject, although it is to be understood the methods described herein are effective with respect to other animals, such as mammals and vertebrate species. More particularly, the term subject can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

Active Compounds

In one embodiment, the invention is directed to compounds or the use as described herein of such compounds of Formula I, I', or I";

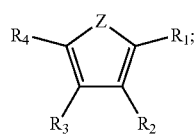
I

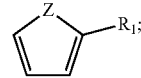
I'

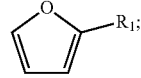
I"

wherein;

each Z is independently O, S or $NR_5$;

wherein $R_1$, $R_2$, $R_3$ and $R_4$, are the same or different, separately represent a hydrogen atom, a $C_1$-$C_{35}$ alkyl radical, advantageously $C_{10}$-$C_{22}$, more advantageously $C_{12}$-$C_{20}$, further advantageously $C_{13}$-$C_{17}$; a $C_1$-$C_{35}$ alkenyl radical, advantageously $C_{10}$-$C_{22}$, more advantageously $C_{12}$-$C_{20}$, further advantageously $C_{13}$-$C_{17}$; or a $C_1$-$C_{35}$ alkynyl radical, advantageously $C_{10}$-$C_{22}$, more advantageously $C_{12}$-$C_{20}$, further advantageously $C_{13}$-$C_{17}$, and wherein the alkyl, alkenyl or alkynyl moiety is optionally substituted with one or more halogens (F, Cl, Br, or I, and more typically F) and/or by one or more moieties selected from the group consisting of epoxide (e.g., an oxygen divalently linked to the carbon chain), hydroxyl or protected hydroxyl ($OR_5$), thiol or protected thiol ($SR_5$), amine ($NR_5R_6$), aldehyde (—CHO), ketone (—$COR_5$), acetyl (—O—CO—$R_5$), or ester (—C(O)$OR_5$) function and wherein $R_5$ and $R_6$ separately represent a hydrogen atom, a $C_1$-$C_{35}$, more typically a $C_1$ to $C_{20}$ alkyl radical, advantageously $C_{10}$-$C_{22}$, more advantageously $C_{12}$-$C_{20}$, further advantageously $C_{13}$-$C_{17}$, or a $C_1$-$C_{35}$ alkenyl radical, advantageously $C_{10}$-$C_{22}$, more advantageously $C_{12}$-$C_{20}$, or further advantageously $C_{13}$-$C_{17}$.

In some embodiments, the compound has Formula I(a):

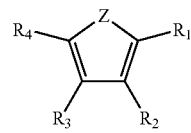

wherein;

Z is independently O, S, $NR_5$;

$R_1$=$R_2$=$R_3$=H;

$R_4$=$C_{13}$-$C_{19}$ alkyl optionally substituted as defined above.

In some embodiments, the compound has Formula I(b):

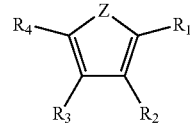

wherein;

Z is independently O, S, $NR_5$;

$R_1$=$R_2$=$R_3$=H;

$R_4$ is a straight $C_9$-$C_{20}$ unsaturated alkyl chain with a single double bond of the formula —CH=CH(CH$_2$)$_m$CH$_3$;

optionally substituted as defined above;

wherein;

m=6 to 17.

In some embodiments, the compound has Formula I(c):

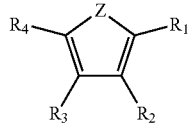

wherein;
Z is independently O, S, NR$_5$;
R$_1$=R$_2$=R$_3$=H;
R$_4$ is a straight C$_{13}$-C$_{19}$ unsaturated alkyl chain with a single double bond of the formula —CH=CH(CH$_2$)$_m$CH$_3$;
optionally substituted as defined above;
wherein;
m=10 to 16.

In some embodiments, the compound has Formula I(d):

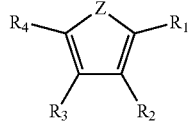

wherein;
Z is independently O, S, NR$_5$;
R$_1$=R$_2$=R$_3$=H;
R$_4$ is a straight C$_9$-C$_{20}$ unsaturated alkyl chain with a single double bond of the formula —(CH$_2$)$_n$—CH=CH(CH$_2$)$_m$CH$_3$;
optionally substituted as defined above;
wherein
n=1 to 17;
m=1 to 17.

In some embodiments, the compound has Formula I(e):

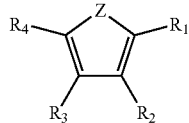

wherein;
Z is independently O, S, NR$_5$;
R$_1$=R$_2$=R$_3$=H;
R$_4$ is a straight C$_{13}$-C$_{19}$ unsaturated alkyl chain with a single double bond of the formula —(CH$_2$)$_n$—CH=CH(CH$_2$)$_m$CH$_3$;
optionally substituted as defined above;
wherein
n=1 to 15;
m=1 to 15.

In some embodiments, the compound has Formula I(f):

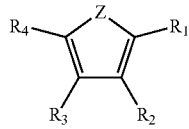

wherein;
Z is independently O, S, NR$_5$;
R$_1$=R$_2$=R$_3$=H;
R$_4$ is a straight C$_9$-C$_{20}$ unsaturated alkyl chain with a single double bond of the formula —(CH$_2$)$_m$CH=CH$_2$;
optionally substituted as defined above;
wherein;
m=7 to 18.

In some embodiments, the compound has Formula I(g):

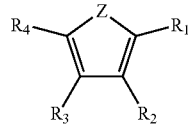

wherein;
Z is independently O, S, NR$_5$;
R$_1$=R$_2$=R$_3$=H;
R$_4$ is a straight C$_{13}$-C$_{19}$ unsaturated alkyl chain with a single double bond of the formula —(CH$_2$)$_m$CH=CH$_2$;
optionally substituted as defined above;
wherein;
m=11 to 17.

In some embodiments, the compound has Formula I(h):

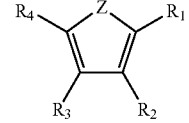

wherein;
Z is independently O, S, NR$_5$;
R$_1$=R$_2$=R$_3$=H;
R$_4$ is a C$_9$-C$_{20}$ alkyl chain comprising two or more double bonds optionally substituted as defined above.

In some embodiments, the compound has Formula I(i):

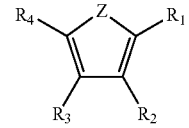

wherein;
Z is independently O, S, NR$_5$;
R$_1$=R$_2$=R$_3$=H;
R$_4$ is a C$_{13}$-C$_{19}$ alkyl chain comprising two or more double bonds optionally substituted as defined above.

In some embodiments, the compound has Formula I(j):

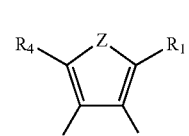

wherein;
Z is independently O, S, NR$_5$;
R$_1$=R$_2$=R$_3$=H;
R$_4$ is a C$_9$-C$_{20}$ alkyl chain comprising one or more triple bonds optionally substituted as defined above.

In some embodiments, the compound has Formula I(k):

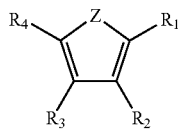

wherein;
Z is independently O, S, NR$_5$;
R$_1$=R$_2$=R$_3$=H;
R$_4$ is a C$_{13}$-C$_{19}$ alkyl chain comprising one or more triple bonds optionally substituted as defined above.

In some embodiments, the compound has Formula 4l):

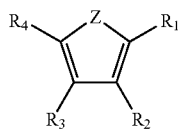

wherein;
Z is independently O, S, NR$_5$;
R$_1$=R$_2$=R$_3$=H;
R$_4$ is a C$_9$-C$_{20}$ alkyl chain comprising one or more double bonds and one or more triple bonds optionally substituted as defined above.

In some embodiments, the compound has Formula I(m):

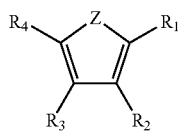

wherein;
Z is independently O, S, NR$_5$;
R$_1$=R$_2$=R$_3$=H;
R$_4$ is a C$_{13}$-C$_{19}$ alkyl chain comprising one or more double bonds and one or more triple bonds optionally substituted as defined above.

In an alternative embodiment, the furan, thiophene or pyrrole can be fused to another heterocyclic or heteroaromatic moiety to produce a multi-ring core, for example, benzofuran, benzothiophene, or indole, which may optionally be substituted with one or more functional groups, preferably with one or more alkyl, alkoxy, halo, or hydroxy substituents.

In one embodiment, the compound has Formula I(n):

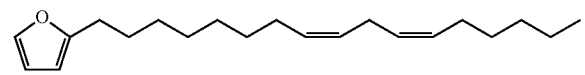

In one embodiment, the compound has Formula I(o):

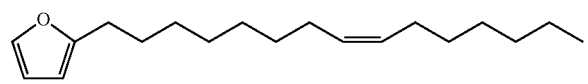 [SMILES: CCCCCC/C=C\CCCCCCCc1ccco1]

In one embodiment, the compound has Formula I(p):

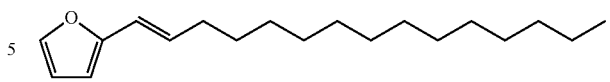

In one embodiment, the compound has Formula I(q):

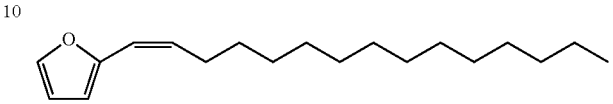

In one embodiment, the compound has Formula I(r):

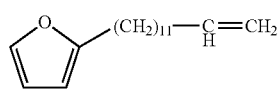

In one embodiment, the compound has Formula I(s):

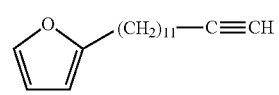

In one embodiment, the compound has Formula I(t):

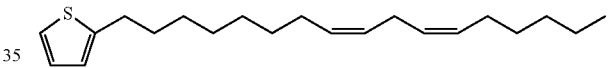

In one embodiment, the compound has Formula I(u):

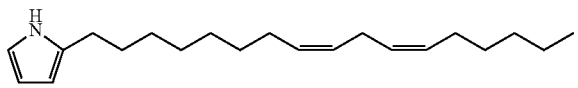 [SMILES: CCCCC/C=C\C/C=C\CCCCCCCc1ccc[nH]1]

In one embodiment, the compound has Formula I(v):

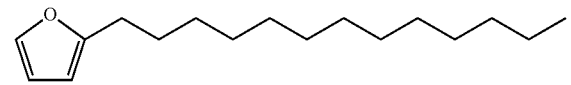 [SMILES: CCCCCCCCCCCCCc1ccco1]

In one embodiment, the compound has Formula I(w):

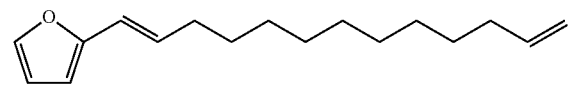

In one embodiment, the compound has Formula I(x):

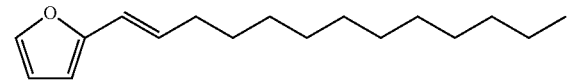

In one embodiment, the compound has Formula I(y):

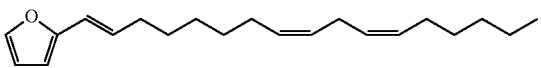

In one embodiment, the compound has Formula I(z):

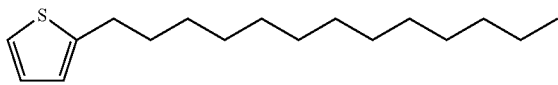

In one embodiment, the compound has the Formula I(aa):

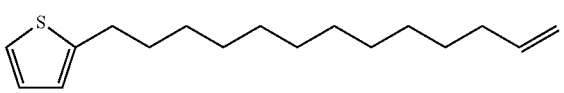 [SMILES: C=CCCCCCCCCCCCc1cccs1]

In one embodiment, the compound has the Formula I(ab):

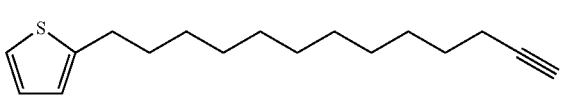 [SMILES: C#CCCCCCCCCCCCc1cccs1]

In one embodiment, the compound has the Formula I(ac):

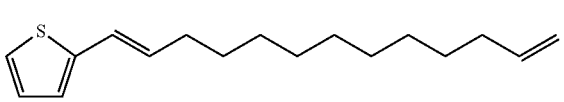

In one embodiment, the compound has the Formula I(ad):

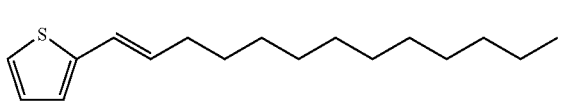

In one embodiment, the compound has the Formula I(ae):

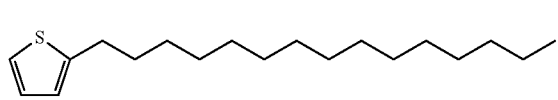 [SMILES: CCCCCCCCCCCCCCCc1cccs1]

In one embodiment, the compound has the Formula I(af):

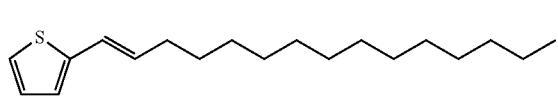

In one embodiment, the compound has the Formula I(ag):

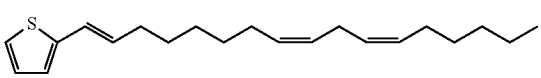 [SMILES: CCCCC/C=C\C/C=C\CCCCC/C=C/c1cccs1]

In one embodiment, the compound has the Formula I(ah):

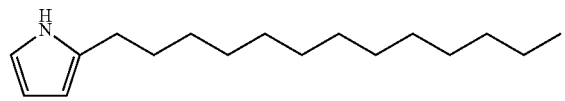 [SMILES: CCCCCCCCCCCCCc1ccc[nH]1]

In one embodiment, the compound has the Formula I(ai):

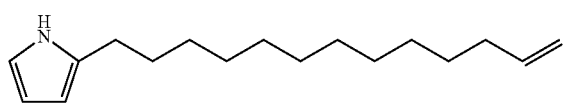 [SMILES: C=CCCCCCCCCCCCc1ccc[nH]1]

In one embodiment, the compound has the Formula I(aj):

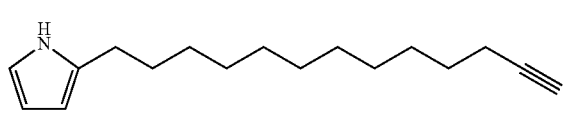 [SMILES: C#CCCCCCCCCCCCc1ccc[nH]1]

In one embodiment, the compound has the Formula I(ak):

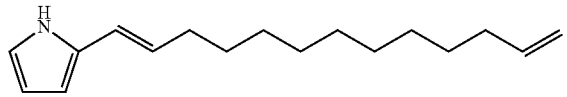 [SMILES: C=CCCCCCCCCC/C=C/c1ccc[nH]1]

In one embodiment, the compound has the Formula I(al):

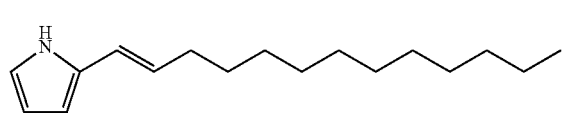 [SMILES: CCCCCCCCCCC/C=C/c1ccc[nH]1]

In one embodiment, the compound has the Formula I(am):

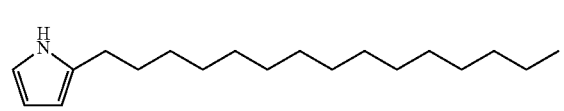 [SMILES: CCCCCCCCCCCCCCCc1ccc[nH]1]

In one embodiment, the compound has the Formula I(an):

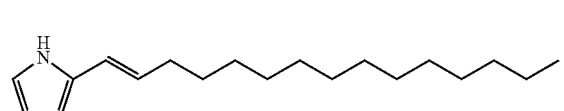

In one embodiment, the compound has the Formula I(ao):

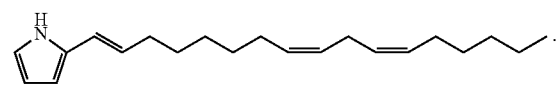

In one embodiment, the compound has the Formula I(ap):

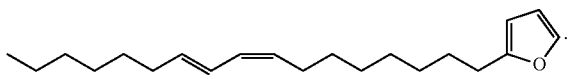 [SMILES: CCCCCC/C=C/C=C\CCCCCCCc1ccco1]

In one embodiment, the compound has the Formula I(aq):

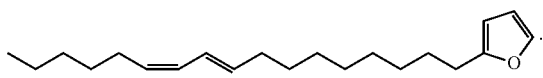 [SMILES: CCCCC/C=C\C=C\CCCCCCCCc1ccco1]

In one embodiment the compound of Formula I is 2-(nonanyl)furan.

In one embodiment the compound of Formula I is 2-(dodecyl)furan.

In one embodiment the compound of Formula I is 2-(tridecyl)furan.

In one embodiment the compound of Formula I is 2-(tetradecyl)furan.

In one embodiment the compound of Formula I is 2-(pentadecyl)furan,

In one embodiment the compound of Formula I is 2-(hexadecyl)furan,

In one embodiment the compound of Formula I is 2-(heptadecyl)furan

In one embodiment the compound of Formula I is 2-(octadecyl)furan).

In one embodiment the compound of Formula I is 2-(nonadecyl)furan).

In one embodiment the compound of Formula I is 2-(8Z-pentadecenyl)furan.

In one embodiment the compound of Formula I is 2-(1E-pentadecenyl)furan.

In one embodiment the compound of Formula I is 2-(1Z-pentadecenyl)furan.

In one embodiment the compound of Formula I is 2-(12-tridecenyl)furan.

In one embodiment the compound of Formula I is 2-(8Z,11Z-heptadecadienyl)furan.

In one embodiment the compound of Formula I is 2-(8Z,11Z-heptadecadienyl)thiophene.

In one embodiment the compound of Formula I is 2-(8Z,11Z-heptadecadienyl)pyrrole.

In one embodiment, the compound of Formula I is 2-(8Z,10E)-heptadecadienyl)furan.

In one embodiment, the compound of Formula I is 2-(9E,11Z-heptadecadienyl)furan.

In one embodiment the compound of Formula I is lignoceric furan.

In one embodiment the compound of Formula I is lauroleic furan.

In one embodiment the compound of Formula I is palmitoleic furan.

In one embodiment the compound of Formula I is cis-vaccenic furan.

In one embodiment the compound of Formula I is erucic furan.

In one embodiment the compound of Formula I is nervonic furan.

In one embodiment the compound of Formula I is arachidonic furan.

In one embodiment the compound of Formula I is crepenynic furan.

Isotopic Substitution

The present invention includes compounds and the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments, it is deuterium that is 90, 95 or 99% enriched at a desired location.

Atrophic Vaginitis

In one embodiment provided herein is a method of treating and/or preventing atrophic vaginitis, comprising administering an effective amount of a compound described herein.

In one embodiment of the invention, a compound for the treatment of atrophic vaginitis is selected from the compounds of Formula I, I', or I" as described herein, or a pharmaceutically acceptable composition, salt, isotopic analog, or prodrug thereof. In one non-limiting example, the atrophic vaginitis is treated with a compound of any of I(a)-I(m), or a pharmaceutically acceptable composition, salt, isotopic analog, or prodrug thereof. In one non-limiting example, the atrophic vaginitis is treated with a compound of Table 1 as described herein, or a pharmaceutically acceptable composition, salt, isotopic analog, or prodrug thereof. In one embodiment, the compound administered is selected from the group consisting of Compound I(n), Compound I(ap), or Compound I(aq) as described herein, or a pharmaceutically acceptable composition, salt, isotopic analog, or prodrug thereof.

According to this invention, the active ingredient is not provided as a botanical extract mixture or combination, but instead the active compound is delivered in a highly pure form. In one embodiment, the invention is a dosage form for the treatment of atrophic vaginitis, wherein the active compound has a purity of at least 96%, 97%, 98%, or 99%, without respect to fillers, stabilizers, or other inert or inactive ingredients. In an alternative embodiment, the dosage form has two or more active ingredients, wherein only one of the active ingredients is selected from compounds of Formula I, I' or I" as described herein. In a further alternative embodiment, the dosage form has two or more active ingredients selected from compounds of Formula I, I', or I" as described herein, wherein each active compound has a purity of at least 96%, 97%, 98%, or 99%, without respect to fillers, stabilizers, or other inert or inactive ingredients.

Atrophic Vaginitis Combination Therapies

In one aspect of the invention, the compounds disclosed herein can be beneficially administered in combination with one or more estrogenic agents used to treat atrophic vaginitis in order to provide beneficial, additive or synergistic effect. Therapies used for the treatment of atrophic vaginitis include, but are not limited to, Estradiol Vaginal Cream, Estradiol Vaginal (local), Conjugated Estrogens, Estradiol Transdermal, Estradiol, Estradiol Patch, Estradiol topical (for use on skin), Estradiol and Norethindrone, Estradiol Valerate, Estradiol Cypionate, Conjugated Estrogens (synthetic a), Conjugated Estrogens (oral), Esterified Estrogens, Conjugated Estrogens and Medroxyprogesterone, and Estropipate.

Pharmaceutical Compositions and Dosage Forms

In one aspect, the invention provides a pharmaceutical composition comprising a pharmaceutically effective amount of the compounds of the present invention and a pharmaceutically acceptable carrier.

The compounds provided herein are administered for medical therapy in a therapeutically effective amount. The amount of the compounds administered will typically be determined by a physician, in the light of the relevant circumstances, including the condition to be treated, the chosen route of administration, the compound administered, the age, weight, and response of the individual patient, the severity of the patient's symptoms, and the like.

The pharmaceutical compositions provided herein can be administered by a variety of routes including oral, parenteral, rectal, subcutaneous, intravenous, intramuscular, and intranasal with a pharmaceutical carrier suitable for such administration. In one embodiment, the compound is administered in a controlled release formulation. In one embodiment, the compound is administered as a topical suppository.

The compositions for oral administration can take the form of bulk liquid solutions or suspensions, or bulk powders. Typically, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (as a nonlimiting example, from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art.

The above-described components for orally administrable or injectable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in Remington's Pharmaceutical Sciences.

In certain embodiments, the formulation comprises water. In another embodiment, the formulation comprises a cyclodextrin derivative. In certain embodiments, the formulation comprises hexapropyl-β-cyclodextrin. In a more particular embodiment, the formulation comprises hexapropyl-β-cyclodextrin (10-50% in water).

The preferred manner of administration is topical, that is, local administration of solutions, gels, lotions and the like to the affected area, including suppository insertion, for example, a vaginal suppository insertion. Conventional, pharmaceutically acceptable carriers include conventional emulsifiers, such as fatty alcohols, glycol ethers and esters of fatty acids; conventional emollients, such as isopropyl and butyl esters of fatty acids, e.g., isopropyl myristate, glycerin, propylene glycol and alcohols; oils such as mineral oil, petroleum oil, oil extracts from animal or vegetable sources; conventional stabilizers including antioxidants and preservatives. The vegetable oil carrier may be selected from any commonly produced for human use; a preferred carrier is unrefined purified avocado oil. The formulation may also include agents, such as urea, to improve the hydration of the vagina.

The present invention also includes pharmaceutically acceptable acid addition salts of compounds of the compounds of the invention. The acids which are used to prepare the pharmaceutically acceptable salts are those which form non-toxic acid addition salts, i.e. salts containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

Synthesis

Preparation of Active Compounds:

The compounds described herein can be prepared by methods known by those skilled in the art. In one non-limiting example the disclosed compounds can be made by the following schemes.

Scheme 1

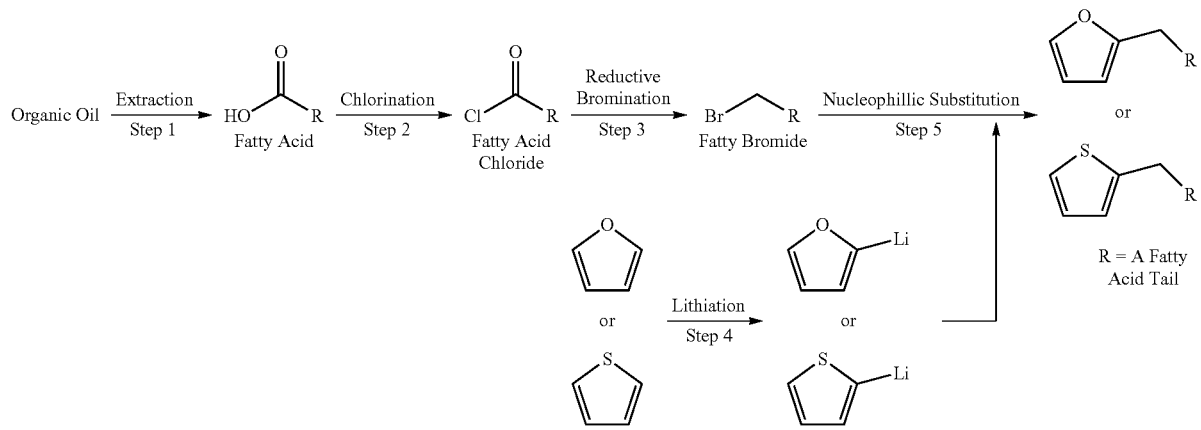

In Scheme 1, Step 1, a Fatty Acid is extracted from an organic oil. In Step 2, the Fatty Acid is chlorinated as known in the art to afford a Fatty Acid Chloride. In Step 3, the Fatty Acid Chloride is brominated and reduced to afford a Fatty Bromide. In Step 4, a lithiated furan or thiofuran is produced by lithiation of the parent furan or thiofuran. In Step 5, the Fatty Bromide undergoes nucleophilic substitution by the previously formed lithiated species to afford a compound of the present invention.

In an alternative embodiment, the Fatty Acid is directly converted to a Fatty Bromide.

Scheme 2

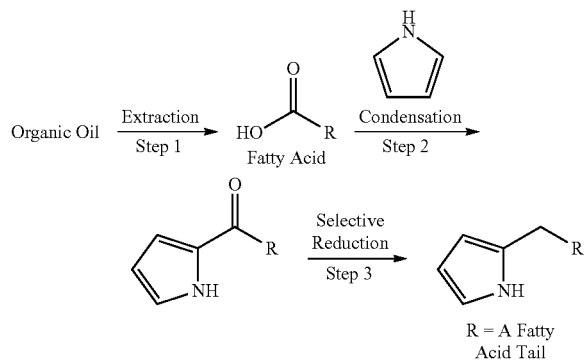

In Scheme 2, Step 1, a Fatty Acid is extracted from an organic oil. In Step 2, the Fatty Acid is condensed with pyrolle as known in the art to afford a pyrollo-ketone. In Step 3, the pyrollo-ketone is selectively reduced to afford a compound of the present invention.

Scheme 3

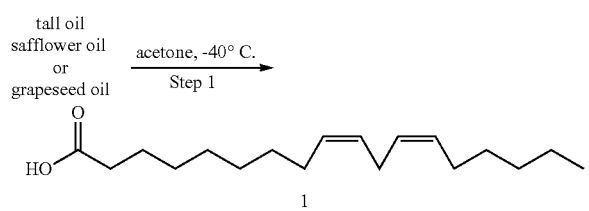

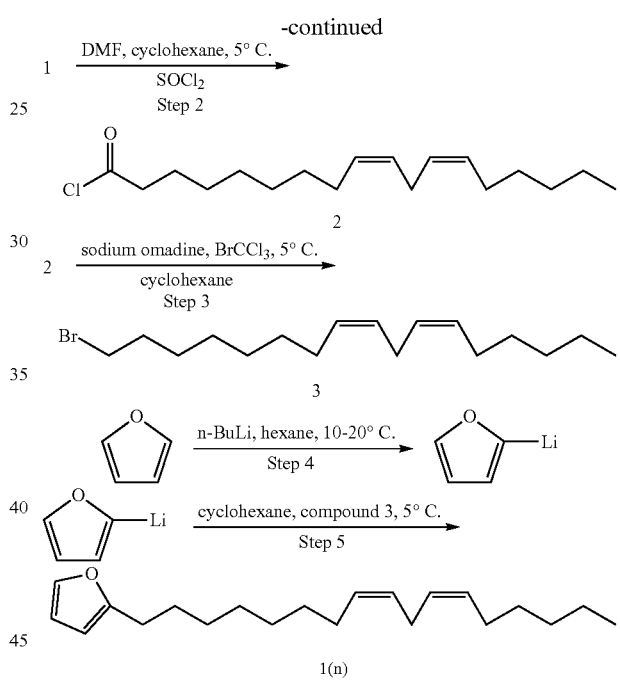

In Scheme 3, Step 1, tall oil or safflower oil is derived to fatty acids and crystalized from an organic solvent such as acetone at reduced temperature to generate non-conjugated linoleic acid (compound 1). In Step 2, compound 1 is dissolved in cyclohexane and thionyl chloride and catalytic DMF is added dropwise at reduced temperature to afford compound 2. In Step 3, compound 2 is subjected to sodium omadine and BrCCl₃ at reduced temperature to afford compound 3. In Step 4, a lithiated furan is generated by directly reacting furan with n-butyllithium. In Step 5, the lithiated furan is reacted with compound 3 to afford compound 1(n).

Scheme 4

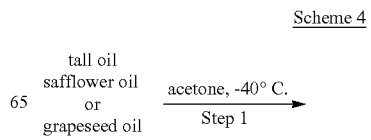

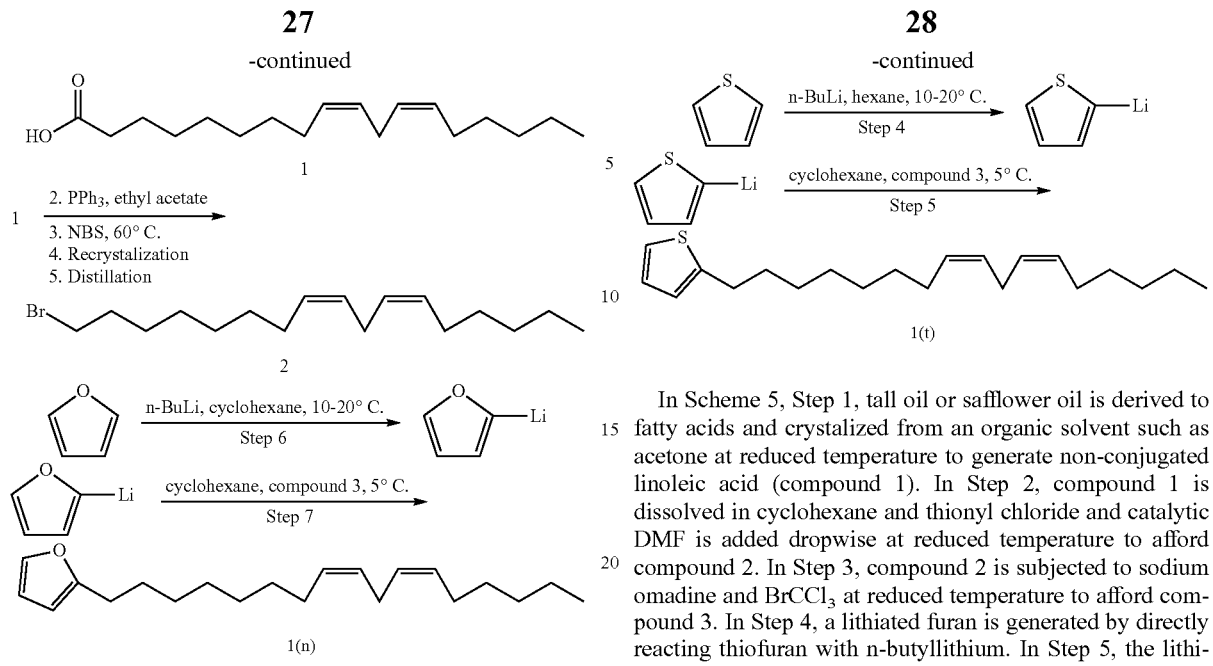

In Scheme 4, Step 1, tall oil, safflower oil or grapeseed oil is derived to fatty acids and crystallized from an organic solvent such as acetone at reduced temperature to generate non-conjugated linoleic acid. In Step 2, equal molar quantities of the resulting linoleic acid and triphenylphosphine are combined in an inert organic solvent such as ethyl acetate until a clear solution is evident. In Step 3, an equimolar quantity of N-bromosuccinimde is added portionally and brought to 60° C. while stirring vigorously for 30 minutes. In Step 4, the mixture is held at 0 C for 8 hours and then fast filtered. In Step 5, the resulting bromodiene is distilled from the ethyl acetate portion of the filtrate. In Step 6, a lithiated furan is generated by directly reacting furan with n-butyllithium in cyclohexane. In Step 7, lithiated n-butyllithium is directly reacted with the bromidiene from Step 5 to generate compound 1(n).

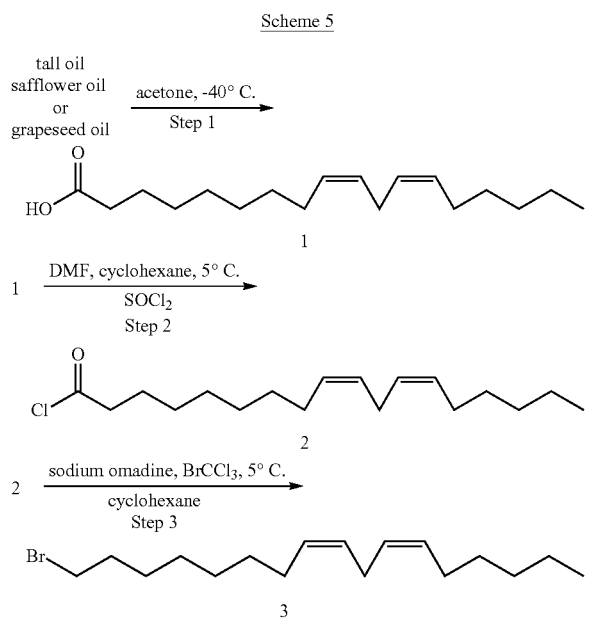

In Scheme 5, Step 1, tall oil or safflower oil is derived to fatty acids and crystalized from an organic solvent such as acetone at reduced temperature to generate non-conjugated linoleic acid (compound 1). In Step 2, compound 1 is dissolved in cyclohexane and thionyl chloride and catalytic DMF is added dropwise at reduced temperature to afford compound 2. In Step 3, compound 2 is subjected to sodium omadine and BrCCl₃ at reduced temperature to afford compound 3. In Step 4, a lithiated furan is generated by directly reacting thiofuran with n-butyllithium. In Step 5, the lithiated thiofuran is reacted with compound 3 to afford compound 1(t).

Scheme 6 tall oil
safflower oil
or          acetone, -40° C.
grapeseed oil   Step 1

[Structure of compound 1: linoleic acid]

1  2. PPh₃, ethyl acetate
   3. NBS, 60° C.
   4. Recrystalization
   5. Distillation

[Structure of compound 2: bromodiene]

[Thiophene] → n-BuLi, cyclohexane, 10-20° C. / Step 6 → [2-lithiothiophene]

[2-lithiothiophene] → cyclohexane, compound 3, 5° C. / Step 7 → [Structure 1(t)]

In Scheme 6, Step 1, tall oil or safflower oil or grapeseed oil is derived to fatty acids and crystalized from an organic solvent such as acetone at reduced temperature to generate non-conjugated linoleic acid. In Step 2, equal molar quantities of the resulting linoleic acid and triphenylphosphine are combined in an inert organic solvent such as ethyl acetate until a clear solution is evident. In Step 3, an equimolar quantity of N-bromosuccinimde is added portionally and brought to 60° C. while stirring vigorously for 30 minutes. In Step 4, the mixture is held at 0 C for 8 hours and then fast filtered. In Step 5, the resulting bromodiene is distilled from the ethyl acetate portion of the filtrate. In Step 6, a lithiated thiofuran is generated by directly reacting thiofuran with n-butyllithium in cyclohexane. In Step 7, lithiated n-butyllithium is directly reacted with the bromidiene from Step 5 to generate compound 1(t).

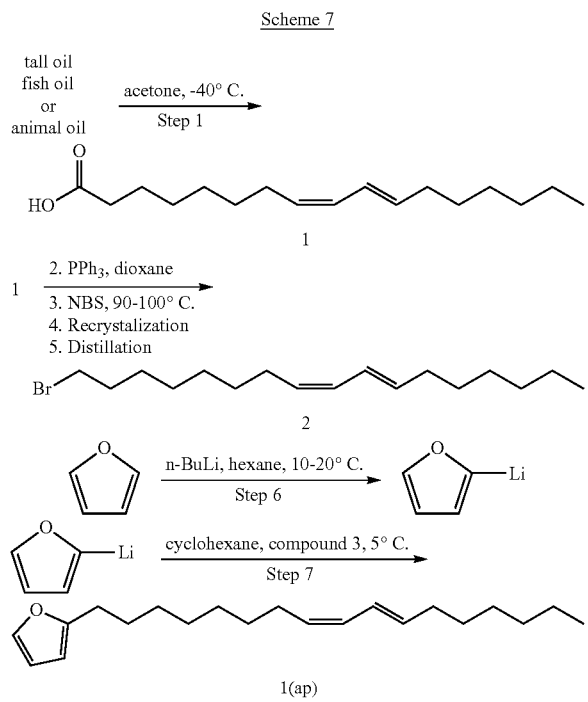

In Scheme 7, Step 1, tall oil or fish oil or animal fat is derived to fatty acids and crystalized from an organic solvent such as acetone at reduced temperature to generate conjugated linoleic acid (compound 1). In Step 2, compound 1 is dissolved in cyclohexane and thionyl chloride and catalytic DMF is added dropwise at reduced temperature to afford compound 2. In Step 3, compound 2 is subjected to sodium omadine and $BrCCl_3$ at reduced temperature to afford compound 3. In Step 4, a lithiated furan is generated by directly reacting furan with n-butyllithium. In Step 5, the lithiated furan is reacted with compound 3 to afford compound 1(ap).

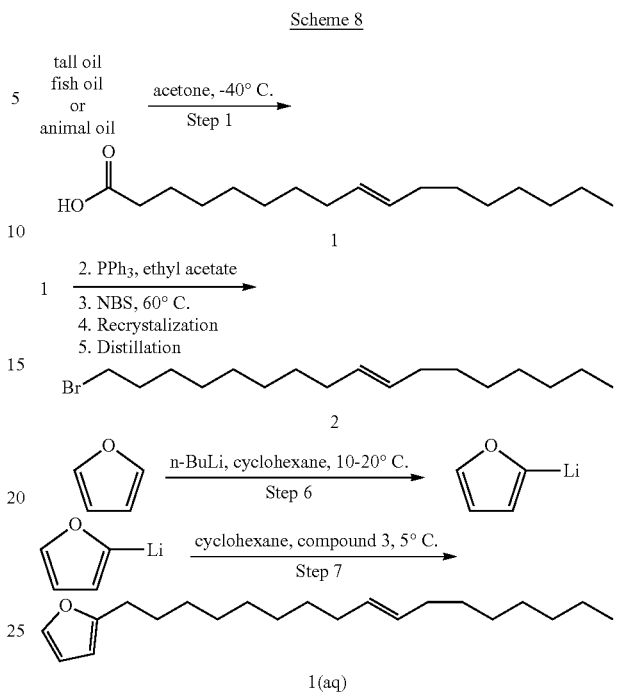

In Scheme 8, Step 1, tall oil or fish oil or animal fat is derived to fatty acids and crystallized from an organic solvent such as acetone at reduced temperature to generate non-conjugated linoleic acid. In Step 2, equal molar quantities of the resulting linoleic acid and triphenylphosphine are combined in an inert organic solvent such as ethyl acetate until a clear solution is evident. In Step 3, an equimolar quantity of N-bromosuccinimide is added portionally and brought to 60° C. while stirring vigorously for 30 minutes. In Step 4, the mixture is held at 0 C for 8 hours and then fast filtered. In Step 5, the resulting bromodiene is distilled from the ethyl acetate portion of the filtrate. In Step 6, a lithiated furan is generated by directly reacting thiofuran with n-butyllithium in cyclohexane. In Step 7, the lithiated furan is directly reacted with the bromidiene from Step 5 to generate compound 1(aq).

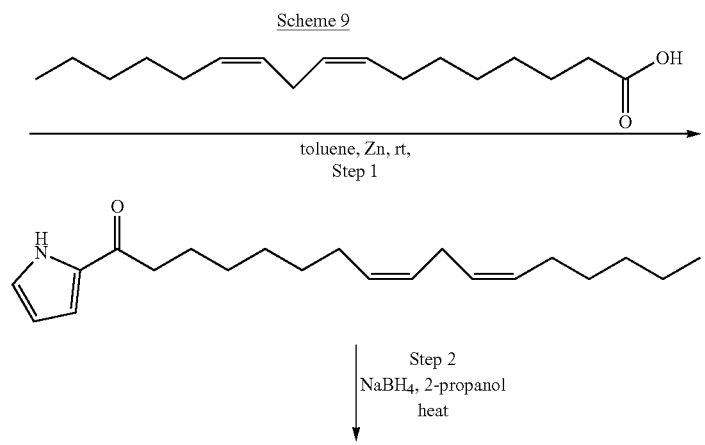

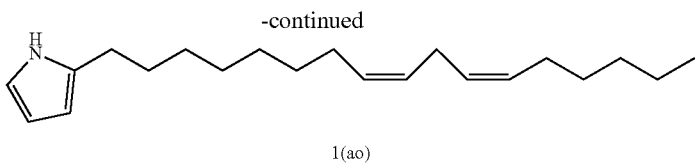

1(ao)

In Scheme 9, pyrrole is directly reacted with an acid in the presence of zinc powder to generate a ketone. In Step 2, the ketone is directly reacted with a reducing agent such as sodium borohydride in a protic solvent such as 2-propanol to afford compound 1(ao).

In another embodiment, compounds of Formula I can be prepared by directly reacting furan or thiophene with an acid chloride using Friedel Craft conditions. The resulting ketone can be reduced with a reducing agent such as sodium borohydride in a protic solvent such as 2-propanol. Alternatively, the ketone can be directly reacted with ethanethiol to generate a thioketal. The thioketal can be reduced using Raney nickel.

In another embodiment, compounds of Formula I can be prepared by directly reacting furaldehyde or thiophenaldehyde with a Wittig reagent to generate an alkene derivative.

In another embodiment, 2-(tri-n-butylstannyl)pyrrole and an acid chloride can be directly reacted using Stille coupling conditions, See, Mohamed, Y. M. A. and Hansen, T. V., Synthesis of mycalazol and mycalazal analogs with potent antiproliferating activities, Purr. Appl. Chem., 83:489-493, 2011. The resulting ketone can be reduced to the corresponding alkane by directly reacting the ketone with palladium on carbon under a hydrogen atmosphere in a protic solvent such as ethanol and an acid catalyst such as sulfuric acid.

EXAMPLES

Example 1

Synthesis of 2-(8Z,11Z-heptadecadienyl)furan
(Scheme 3)

Step 1. Preparation of High Purity Linoleic Acid

A1) Obtain conjugated ("c") and preferentially non-conjugated ("nc") linoleic acid ($C_{18}$) sourced from natural grapeseed (60% nc-10% c) or safflower (60% nc-10% c).
B) Mix vegetable oil with purified water 2:1 to which has been added 0.5% wt/wt of *Candida rugosa* enzymes (Amano 12K) or use an immobilized enzyme bed and recirculate the water and oil mixture. In both examples maintain temperature at not more than 40° C. and not less than 35° C. under a nitrogen blanket. If enzymes are freely mixed then held at mixing that allows complete recirculation of container contents every 60 seconds and continue for 24 hours. Discontinue reaction and add heptane or other non-polar solvent to solution (approx 0.5:1 ratio), stir and decant under nitrogen and low light. Repeat three times to obtain the fatty acids. Evaporate solvent under nitrogen.
A2) Alternately and preferentially obtain Tall Oil fatty acids that are predominately linoleic (75%) distributed as 90% non-conjugated and 10% conjugated.
C) Mix the fatty acids obtained in B or in A2 and mix with acetone in a ratio of 1 part fatty acid to 3 parts acetone (weight:weight) and bring to −76° C. from 1 to 6 hours and hold for 24 hours at −76° C.
D) Vacuum filter using nominal 5-15 micron filter while chilled at less than −70° C. Repeat low temperature crystallization until acetone is clear after 24 hours. Evaporate solvent to recover high purity linoleic acid
E) Recover 99% pure linoleic acid (non-conjugated) with flash chromatography or critical fluids chromatography using standard separation protocols.

Step 2. Preparation of Bromodiene

A) Add equimolar parts of linoleic acid and triphenylphosphine to ethyl acetate and stir under a nitrogen flow until a clear solution is obtained.
B) Add portionally an equimolar part of N-bromosuccinimide and bring to 60 C and hold for 30 minutes with good stirring.
C) Bring solution to 0 C and hold for 8 hours then fast filter to recover filtrant
D) Distill by short path the acyl bromide product to obtain bromodiene.
E)) Bromodiene may be further treated chromatographically to obtain greater purity.

Step 3: Preparation Lithiated Furan

A) Prepare a 1M solution of butyllithium in cyclohexane. Note: do not chill below negative 10° C. to prevent congealing.
B) Add butyllithium in hexane dropwise at approximately 3-4 ml/min to furan/THF (or cyclohexane) solution. Note color change to yellow.
C) Stir for not longer than 2 hours after all butyllithium has been added. The lithiated furan is obtained in a 90% yield.

Step 4: Synthesis of
2-(8Z,11Z-heptadecadienyl)furan

A) Add approximately 1 part cyclohexane and 1 part bromodiene from Step 2 together and begin nitrogen flow.
B) Add lithiated furan from Step 3 dropwise.
C) Note color change to dark reddish brown and then maintain stirring and nitrogen for 24 hours.
E) Wash product three times with 3% saline solution mixed with isopropanol or ethanol (1:1) and decant, evaporate solvent.
F) Purify with chromatography.

Example 2

Synthesis of 2-(8Z,11Z-heptadecadienyl)thiophene
(Scheme 5)

Steps 1-3 are Carried Out as Described in Example 1

Step 4: Synthesis of Lithiated Thiophene

A) Prepare a 1M solution of butyllithium in hexane. Note: do not chill below 10° C. to prevent congealing.

B) Add thiopene to cyclohexane.
C) Add butyllithium in cyclohexane dropwise to thiopene/cyclohexane solution.
E) Stir for not longer than 2 hours after all butyllithium has been added.
F) Work up in standard manner to obtain product.

Step 5: Synthesis of
2-(8Z,11Z-heptadecadienyl)thiophene

A) Add approximately 1 part cyclohexane and 1 part bromodiene from Step 3 together and begin nitrogen flow.
B) Add lithiated thiophene from Step 4 dropwise.
C) After all lithiated thiopene has been added maintain stirring and nitrogen for 24 hours.
E) Wash product three times with 3% saline solution mixed with isopropanol or ethanol (1:1) and decant, evaporate solvent.
F) Purify with chromatography. The product was obtained in a 85% yield.

Example 3

Synthesis of 2-(8Z,11Z-heptadecadienyl)pyrrole
(Scheme 9)

Step 1

A mixture of pyrrole (2.0 g, 29.8 mmol) 8Z,11Z-hexadecadienoic acid (17.83 g, 44.7 mmol) and zinc powder (3.88 g, 59.7 mmol) in toluene (75 ml) is stirred at room temperature until the pyrrole is no longer detectable by thin layer chromatography or HPLC. The reaction is quenched with saturated sodium bicarbonate solution (50 ml) and extracted with ethyl acetate (3×30 ml). The combined organic layers are washed with water, dried over anhydrous $Na_2SO_4$, filtered and concentrated in vacuo. The product is purified by using silica gel column chromatography that is eluted with a dichloromethane—methanol gradient.

Step 2

To a stirred solution of the ketone from step 1 (1.63 g, 5.18 mmol), in 150 ml of 2-propanol at ambient temperature is slowly added sodium borohydride (1.34 g, 36.26 mmol). The reaction is heated at reflux and monitored by thin layer chromatography or HPLC. Once the starting material is no longer detected, the reaction is poured into 150 ml of ice-water and the solution is acidified with 10% aqueous HCl. The reaction is extracted with dichloromethane (3×50 ml). The combined organic extracts are washed with water, brine, and dried over anhydrous $Na_2SO_4$, filtered and concentrated in vacuo. The product is purified by using silica gel column chromatography that is eluted with a dichloromethane—methanol gradient.

Example 4

2-(8Z,11Z-Heptadecadienyl)furan Formulation

According to one embodiment of the present invention,

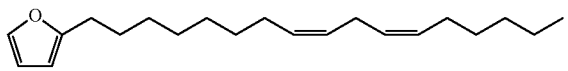

2-(8Z,11Z-heptadecadienyl)furan

This lipidic furan can be composed of the compound mixed in a ratio of 80 parts to 20 parts with other lipidic furans of the general Formula I and this solution added to a vegetable oil base and encapsulated for topical application. The total amount of lipidic furans as expressed as a percent of the finished product can vary from 0.1 to 100%, with a preferred amount at about 3%. The vegetable oil carrier may be selected from any commonly produced for human use; a preferred carrier is unrefined purified avocado oil.

Example 5

Lipidic Furan Formulation

According to another embodiment of the invention,

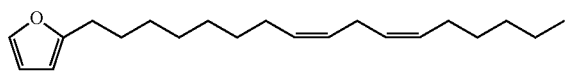

2-(8Z,11Z-heptadecadienyl)furan

The lipidic furan, 2-(8Z,11Z-heptadecadienyl)furan, can be incorporated in a vegetable oil base for topical application. In this instance, it is preferable to provide a greater purity of the compound of not less than 98% in order to ensure consistent and predictable outcome of desired results and to take advantage of its general long term stability. The total amount of the compound as expressed as a percent of the finished product can vary from 0.1 to 100%, with a preferred amount at about 3% for better absorption. The vegetable oil carrier may be selected from any commonly produced for human use; a preferred carrier is unrefined purified avocado oil.

Example 6

2-(8Z,11Z-Heptadecadienyl)thiofuran Formulation

According to one embodiment of the present invention,

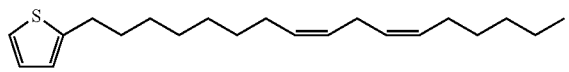 [SMILES: CCCCC/C=C\C/C=C\CCCCCCCc1cccs1]

2-(8Z,11Z-heptadecadienyl)thiofuran

This lipidic thiofuran can be composed of the compound mixed in a ratio of 80 parts to 20 parts with other lipidic furans or thiofurans of the general Formula I and this solution added to a vegetable oil base and encapsulated for topical application. The total amount of lipidic furans or thiofurans as expressed as a percent of the finished product can vary from 0.1 to 100%, with a preferred amount at about 3%. The vegetable oil carrier may be selected from any commonly produced for human use; a preferred carrier is unrefined purified avocado oil.

Example 7

Lipidic Furan Formulation

According to another embodiment of the invention,

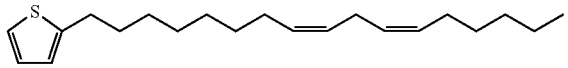

2-(8Z,11Z-heptadecadienyl)thiofuran

The lipidic thiofuran, 2-(8Z,11Z-heptadecadienyl)thiofuran, can be incorporated in a vegetable oil base and encapsulated for topical application. In this instance, it is preferable to provide a greater purity of the compound of not less than 98% in order to ensure consistent and predictable outcome of desired results and to take advantage of its general long term stability. The total amount of the compound as expressed as a percent of the finished product can vary from 0.1 to 100%, with a preferred amount at about 3% for absorption. The vegetable oil carrier may be selected from any commonly produced for human use; a preferred carrier is unrefined purified avocado oil.

Example 8

2-((8Z,11Z)-heptadeca-8,11-dien-1-yl)-1H-pyrrole Formulation

According to one embodiment of the present invention,

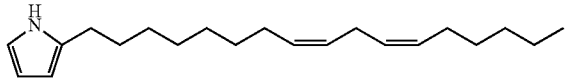

2-((8Z,11Z)-heptadeca-8,11-dien-1-yl)-1H-pyrrole

This lipidic pyrrole can be composed of the compound mixed in a ratio of 80 parts to 20 parts with other lipidic furans thiofurans or pyrroles of the general Formula I and this solution added to a vegetable oil base and encapsulated for topical application. The total amount of lipidic furans thiofurans or pyrroles as expressed as a percent of the finished product can vary from 0.1 to 100%, with a preferred amount at about 3%. The vegetable oil carrier may be selected from any commonly produced for human use; a preferred carrier is unrefined purified avocado oil.

Example 9

Lipidic Pyrrole Formulation

According to another embodiment of the invention,

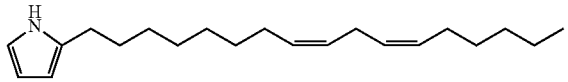 [SMILES: CCCCC/C=C\C/C=C\CCCCCCCc1ccc[nH]1]

The lipidic pyrrole, 2-((8Z,11Z)-heptadeca-8,11-dien-1-yl)-1H-pyrrole, can be incorporated in a vegetable oil base and encapsulated for topical application. In this instance, it is preferable to provide a greater purity of the compound of not less than 98% in order to ensure consistent and predictable outcome of desired results and to take advantage of its general long term stability. The total amount of the compound as expressed as a percent of the finished product can vary from 0.1 to 100%, with a preferred amount at about 3%. The vegetable oil carrier may be selected from any commonly produced for human use; a preferred carrier is unrefined purified avocado oil.

Example 10

2-((8Z,10E)-heptadeca-8,10-dien-1-yl)furan Formulation

According to one embodiment of the present invention,

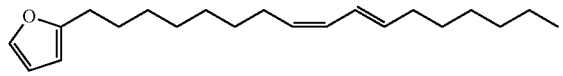 [SMILES: CCCCCC/C=C/C=C\CCCCCCCc1ccco1]

2-((8Z,10E)-heptadeca-8,10-dien-1-yl)furan

This lipidic furan can be composed of the compound mixed in a ratio of 80 parts to 20 parts with other lipidic furans of the general Formula I and this solution added to a vegetable oil base and encapsulated for topical application. The total amount of lipidic furans as expressed as a percent of the finished product can vary from 0.1 to 100%, with a preferred amount at about 3%. The vegetable oil carrier may be selected from any commonly produced for human use; a preferred carrier is unrefined purified avocado oil.

Example 11

Lipidic Furan Formulation

According to another embodiment of the invention,

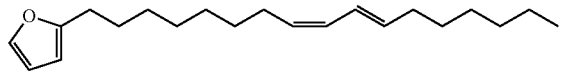

2-((8Z,10E)-heptadeca-8,10-dien-1-yl)furan

The lipidic furan, 2-((8Z,10E)-heptadeca-8,10-dien-1-yl)furan, can be incorporated in a vegetable oil base and encapsulated for topical application. In this instance, it is preferable to provide a greater purity of the compound of not less than 98% in order to ensure consistent and predictable outcome of desired results and to take advantage of its general long term stability. The total amount of the compound as expressed as a percent of the finished product can vary from 0.1 to 100%, with a preferred amount at about 3%. The vegetable oil carrier may be selected from any commonly produced for human use; a preferred carrier is unrefined purified avocado oil.

Example 12

2-((9E,11Z)-heptadeca-9,11-dien-1-yl)furan Formulation

According to one embodiment of the present invention,

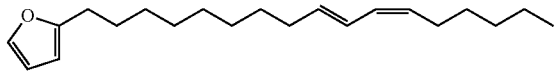 [SMILES: CCCCC/C=C\C=C\CCCCCCCCc1ccco1]

2-((9E,11Z)-heptadeca-9,11-dien-1-yl)furan

This lipidic furan can be composed of the compound mixed in a ratio of 80 parts to 20 parts with other lipidic furans of the general Formula I and this solution added to a vegetable oil base and encapsulated for topical application. The total amount of lipidic furans as expressed as a percent of the finished product can vary from 0.1 to 100%, with a preferred amount at about 3%. The vegetable oil carrier may be selected from any commonly produced for human use; a preferred carrier is unrefined purified avocado oil.

Example 13

Lipidic Furan Formulation

According to another embodiment of the invention,

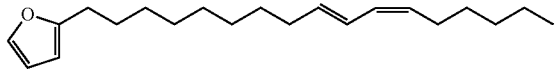

2-((9E,11Z)-heptadeca-9,11-dien-1-yl)furan

The lipidic furan, 2-((9E,11Z)-heptadeca-9,11-dien-1-yl)furan, can be incorporated in a vegetable oil base and encapsulated for topical application. In this instance, it is preferable to provide a greater purity of the compound of not less than 98% in order to ensure consistent and predictable outcome of desired results and to take advantage of its general long term stability. The total amount of the compound as expressed as a percent of the finished product can vary from 0.1 to 100%, with a preferred amount at about 3%. The vegetable oil carrier may be selected from any commonly produced for human use; a preferred carrier is unrefined purified avocado oil.

This specification has been described with reference to embodiments of the invention. The invention has been described with reference to assorted embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the invention.

The invention claimed is:

1. A method for the treatment of atrophic vaginitis in a human, comprising topically administering an effective amount of a compound of Formula I(n):

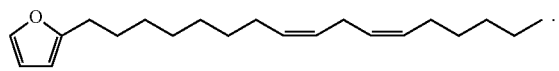 [SMILES: CCCCC/C=C\C/C=C\CCCCCCCc1ccco1]

2. The method of claim 1, wherein the compound is administered as a vaginal suppository.

* * * * *